(12) United States Patent
Johnson

(10) Patent No.: US 7,052,916 B2
(45) Date of Patent: May 30, 2006

(54) POLYPEPTIDE ANALYSES USING STABLE ISOTOPE LABELING

(75) Inventor: Richard S. Johnson, Mercer Island, WA (US)

(73) Assignee: Immunex Corporation, Seattle, WA (US)

( * ) Notice: Subject to any disclaimer, the term of this patent is extended or adjusted under 35 U.S.C. 154(b) by 366 days.

(21) Appl. No.: 10/154,872

(22) Filed: May 24, 2002

(65) Prior Publication Data

US 2003/0219838 A1 Nov. 27, 2003

(51) Int. Cl.
*G01N 33/00* (2006.01)

(52) U.S. Cl. ............................ 436/86; 436/56; 436/57; 436/19; 436/120; 436/173; 436/161; 435/7.1; 435/7.92; 435/24

(58) Field of Classification Search .................... 435/4, 435/7.1, 7.92, 24; 436/120, 173, 161, 119, 436/56, 57, 86
See application file for complete search history.

(56) References Cited

U.S. PATENT DOCUMENTS

| 5,986,061 | A * | 11/1999 | Pestka .......................... 530/352 |
| 6,348,569 | B1 * | 2/2002 | Walker et al. ............... 530/300 |
| 6,391,650 | B1 * | 5/2002 | Anderson et al. ........... 436/174 |
| 6,670,194 | B1 * | 12/2003 | Aebersold et al. .......... 436/173 |
| 2003/0108959 | A1 * | 6/2003 | Johnson et al. ............. 435/7.21 |

OTHER PUBLICATIONS

Kanstrup et al.. Arch Biochem & Biophysics 1993 vol. 304, pp. 332-337.*
Adamczyk, M. et al., "Selective analysis of phosphopeptides within a protein mixture by chemical modification, reversible biotinylation and mass spectrometry," *Rapid Commun. Mass Spectrom.*, 15:1481-1488, 2001.
Byford, M., "Rapid and selective modification of phosphoserine residues catalyzed by $Ba^{2+}$ ions for their detection during peptide microsequencing," *Biochem. J.*, 280:261-265, 1991.
Goshe, M. et al., "Phosphoprotein isotope-coded affinity tag approach for isolating and quantitating phosphopeptides in proteome-wide analyses," *Anal. Chem.*, 73:2578-2586, 2001.

Gygi, S. et al., "Quantitative analysis of complex protein mixtures using isotope-coded affinity tags," *Nature Biotech.*, 17:994-999, 1999.
Jaffe, H. et al., "Characterization of serine and threonine phosphorylation sites in β-elimination/ethanethiol addition-modified proteins by electrospray tandem mass spectrometry and database searching," *Biochem.*, 37:16211-16224, 1998.
Johnson, R. et al., "Isotope Coded Labile Affinity Proteomics," Poster presented at the 49th American Society Mass Spectrometry, on Mass Spectrometry and Allied Topics, in Chicago, IL, May 27-31, 2001.
Oda, Y. et al., "Enrichment analysis of phosphorylated proteins as a tool for probing the phosphoproteome," *Nature Biotech.*, 19:379-382, 2001.
Qian, W. et al., "Phosphoprotein isotope-coded solid-phase tag approach for enrichment and quantitative analysis of phosphopeptides from complex mixtures," *Anal. Chem.*, 75:5441-5450, 2003.
Qiu, Y. et al., "Acid-labile isotope-coded extractants: A class of reagents for quantitative mass spectrometric analysis of complex protein mixtures," *Anal. Chem.*, 74:4969-4979, 2002.
Shen, M. et al., "Isolation and isotope labeling of cysteine- and methionine-containing tryptic peptides," *Molecular & Cellular Proteomics* 2:315-324, 2003.
Spahr, C. et al., "Simplification of complex peptide mixtures for proteomic analysis: Reversible biotinylation of cysteinyl peptides," *Electrophoresis*, 21:1635-1650, 2000.
Weckwerth, W. et al., "Comparative quantification and identification of phosphoproteins using stable isotope labeling and liquid chromatography/mass spectrometry," *Rapid Commun. Mass Spectrom.*, 14:1677-1681, 2000.

* cited by examiner

Primary Examiner—Long V. Le
Assistant Examiner—Jacob Cheu
(74) *Attorney, Agent, or Firm*—Christensen O'Connor Johnson Kindness PLLC

(57) ABSTRACT

Methods for incorporating a stable isotope into a protein or peptide fragment are disclosed. The methods include providing isolated isotope-labeled protein or peptide fragments and analyzing the isolated labeld fragments. In another aspect of the invention, methods for quantitatively comparing peptides in two protein or peptide fragment mixtures are provided. In these methods, protein levels are measured using stable-isotope coded protein or peptide fragments.

12 Claims, 8 Drawing Sheets

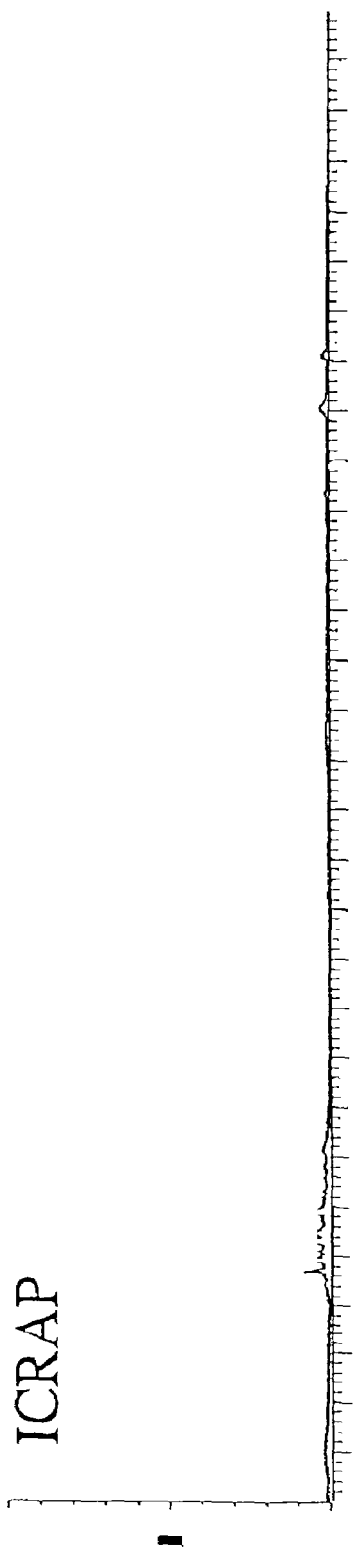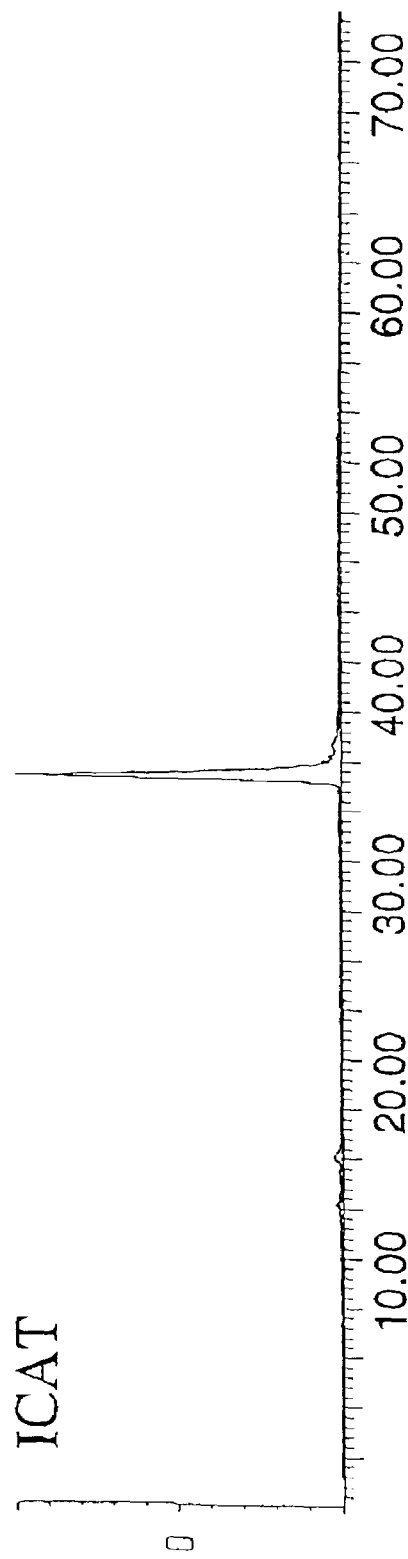
FIGURE 3

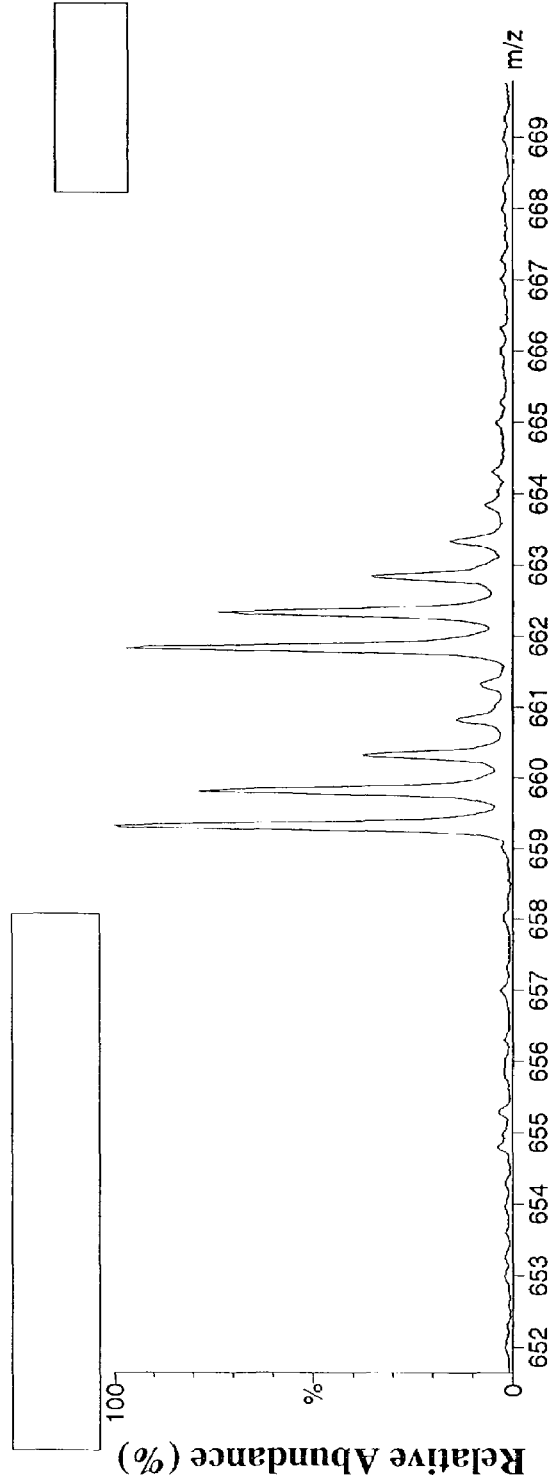
Figure X: The peptide VGINYWLAHK from bovine lactalbumin had been isolated using the Pi³-Trp beads, as described by the manufacturer (BioMolecular Technologies). As part of the isolation chemistry, the indole ring of tryptophan is modified by the addition of a thiol group, which was labeled 1:1 with N-ethyl iodoacetamide and N-d₅-ethyl iodoacetamide.

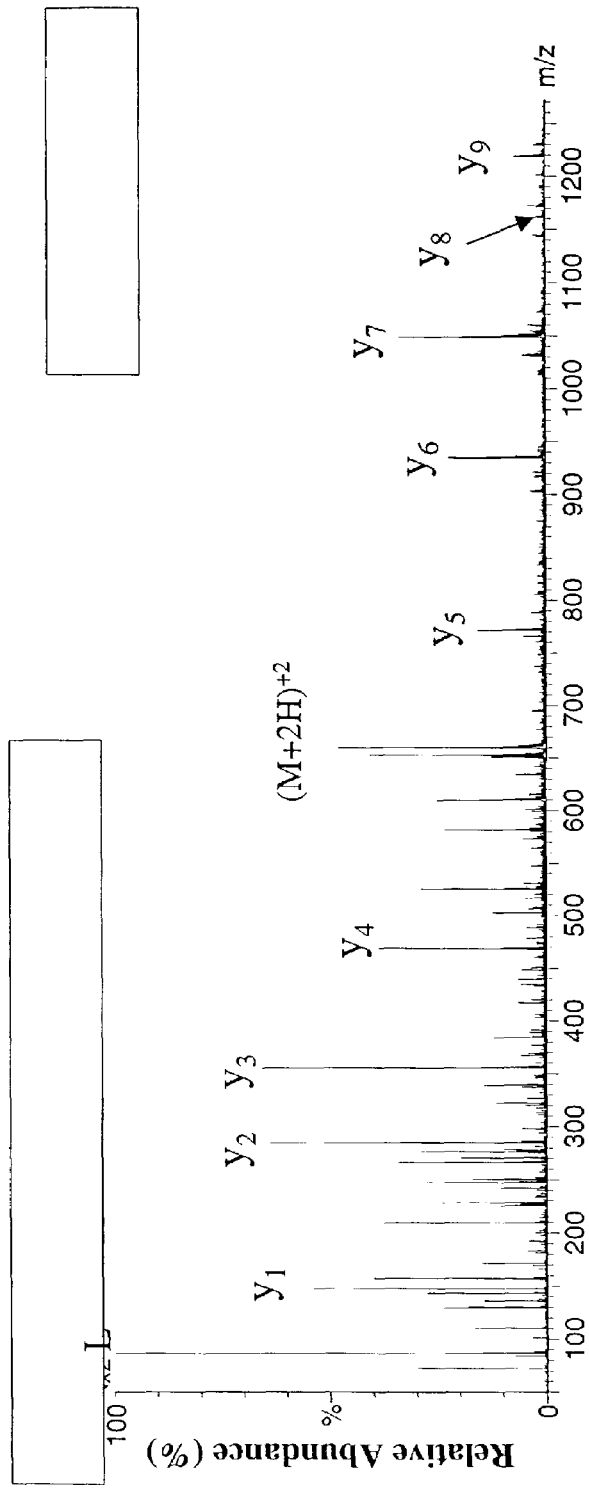

Figure Y: MS/MS spectrum of the peptide VGINYWLAHK from bovine lactalbumin had been isolated using the Pi³-Trp beads, as described by the manufacturer (BioMolecular Technologies). As part of the isolation chemistry, the indole ring of tryptophan is modified by the addition of a thiol group, which was subsequently labeled with N-ethyl iodoacetamide, resulting in a residue mass of 303 u. A contiguous and complete series of sequence-specific fragment ions are present, and the presence of the modified residue does not introduce any high abundance artifact peaks.

POLYPEPTIDE ANALYSES USING STABLE ISOTOPE LABELING

BACKGROUND OF THE INVENTION

1. Field of the Invention

The present invention is relates to proteomics and more specifically involves analyzing polypeptides and peptides using stable isotope labeling techniques coupled with mass spectrometry.

2. Description of Related Art

Proteomics usually involves separating individual proteins using two dimensional gel electrophoresis (2D-PAGE) and comparing stain density. Proteomic analyses using 2D-PAGE can be automated, but only at significant expense requiring automated gel staining and destaining devices, imaging equipment, imaging software, spot cutting robotics, automated in-gel digestion, robotic MALDI plate spotting, and mass spectrometry. Even expensive high throughput 2D-PAGE systems are known to have difficulties with higher molecular weight proteins, membrane proteins, and highly acidic or basic proteins. Despite the high resolution separations of proteins provided by 2D-PAGE, the method still suffers from a limited dynamic range and low abundance proteins are very difficult to detect in the presence of high abundance proteins. Nevertheless, 2D-PAGE has been the state of the art for making quantitative proteomic measurements.

Reversible biotinylation of cysteinyl peptides has been utilized in a method for the rapid identification of components in a protein mixture (Spahr et al., 2000). In a representative method, a protein mixture is digested and the resulting peptide fragment's cysteine residues biotinylated with a cleavable biotinylation reagent (i.e., N-[6-(biotinamido)hexyl]-3'-(2'-pyridyldithio)propionamide, commonly known as "biotin-HPDP"). The biotinylated peptides are then isolated using avidin affinity chromatography and then eluted from the avidin by treatment with dithiothreitol (DTT), which cleaves the link between the biotin and peptide fragment releasing the peptide fragment. The released peptide fragment has free sulfhydryl groups that are alkylated by treatment with iodoacetamide. The alkylated peptide fragments are then analyzed by LC/MS/MS to provide proteomic information. The method described above simplifies complex peptide mixtures for proteomic analysis.

Another analytical method involves labeling proteolytic peptides with different stable isotopes depending on the protein source (e.g., control cells versus stimulated cells). Identical peptides labeled with different isotopes have nearly equivalent chemical properties, so pairs of peptides differing only in the label will elute approximately at the same time and exhibit identical ionization efficiency. The first example of this method was the use of whole cell $^{15}N$ labeling to compare wild type and mutant cell lines. This approach is limited to studies of cultured cells, and the isotope coding involves the incorporation of varying numbers of nitrogen atoms in each peptide, hence varying mass differences from peptide to peptide.

Another approach involves N-terminally labeling proteolytic peptides with isotope-coded nicotinic acid derivatives. This method has a side benefit of directing fragmentation in MS/MS. More recently, whole cell labeling with $^{13}C$ lysine has been shown to be a simple way to introduce a constant mass shift in tryptic peptides.

In addition to the isotope labeling methods noted above, complex protein mixtures have also been quantitatively analyzed using isotope-coded affinity tags and mass spectrometry (Aebersold et al., 1999). The analysis is based on labeling a protein's cysteine residues with an isotope-coded affinity tag (ICAT) and subsequent analysis of the tagged protein, or fragment thereof, by mass spectrometry. The ICAT reagents employ cysteine-specific chemical reactivity, an isotope coded linker, and a biotin affinity tag, and introduce a constant mass difference for each cysteine present in the peptide. The ICAT reagent includes a reactive functional group having specificity toward sulfhydryl groups, a biotin affinity tag, and an isotope labeled linker covalently linking the sulfhydryl reactive group with the biotin tag. An advantage of this method is that complex tryptic peptide mixtures can be simplified by the selective isolation of peptides containing cysteine, which is one of the least common amino acids, thus approaching the ideal of obtaining a single peptide per protein.

In a representative method, the cysteinyl residues in a reduced protein sample representing one cell state are derivatized with one isotopic form (e.g., light form, no isotope label) of the ICAT and the equivalent groups in a second cell state are derivatized with another isotopic form (i.e., heavy form, isotope labeled). The two samples are then combined, enzymatically cleaved to produce peptide fragments, and the biotin tagged fragments isolated by avidin affinity chromatography. The isolated fragments are then released and analyzed by microLC-MS/MS. The quantity and sequence identity of the proteins from which the fragments are derived are determined by automated multistage mass spectrometry. Despite the utility of the ICAT method described above, the method requires the use of the relatively sophisticated and expensive ICAT reagent. Furthermore, the mass spectra of tagged protein fragments is obscured by high intensity ions related to the reagent.

Despite the advances in protein analysis, there exists a need for rapid, reliable, and efficient methods for analyzing complex protein mixtures. The present invention seeks to fulfill this need and provides further related advantages.

SUMMARY OF THE INVENTION

In one aspect, the present invention provides methods for incorporating a stable isotope into a protein or peptide fragment and analyzing the isotope labeled protein or peptide fragment. More particularly, such a method involves causing a protein or peptide fragment to react with an agent that includes one or more stable isotopes to provide an isotope-labeled protein or peptide fragment. In one embodiment, the protein or peptide fragment is an isolated protein or peptide fragment that contains a reactive group capable of reacting with the agent that includes one or more stable isotopes. Such reactive groups can include a cysteinyl residue sulfhydryl group, thiol groups that are introduced into the protein or peptide fragment, or other reactive groups. Thus, the isotope-labeled protein or peptide fragment may be, but is not limited to, a cysteine containing protein or fragment or a tryptophan-containing protein or peptide fragment that is labeled through the protein's or peptide fragment's thiol-modified tryptophan residue.

In one embodiment the protein or peptide fragment for reaction with the isotope-labeled agent is obtained by reacting a cysteinyl residue in a protein or peptide fragment with an affinity reagent, isolating the affinity-labeled protein or peptide fragment on a solid phase, and then releasing the isolated protein or peptide fragment from the solid phase. In one embodiment, the released protein or peptide fragment is the same as the protein or peptide fragment reacted with the affinity reagent.

In another aspect of the invention, methods for measuring protein levels in two protein or peptide fragment mixtures are provided.

In one embodiment of the method, the cysteinyl residues of proteins in first and second protein mixtures are reacted with an affinity reagent to provide first and second affinity-labeled protein mixtures. The first and second affinity-labeled proteins are isolated on a solid phase to provide first and second isolated affinity-labeled proteins. The first and second isolated proteins are released from the solid phase to provide first and second released proteins. The first and second released proteins are then reacted with an isotope-coded agent to provide first and second isotope-coded proteins. The first released proteins are reacted with a first agent that includes one or more stable isotopes. The second released proteins are reacted with a second agent that includes no stable isotopes or fewer stable isotopes than the first agent. The first and second isotope-coded proteins are then analyzed. In one embodiment, the first and second isotope-coded proteins are combined and then analyzed by mass spectrometry. The mass spectral analysis of the first and second isotope-coded proteins provide quantitative information relating to the difference in the amounts (e.g., expression levels) of the proteins in the first and second protein mixtures.

In another embodiment of the method, the cysteinyl residues of proteins in first and second protein mixtures are reacted with an affinity reagent to provide first and second affinity-labeled protein mixtures. The first and second affinity-labeled protein mixtures are then digested to provide peptide fragments, those containing cysteinyl residues being affinity labeled. The first and second affinity-labeled peptide fragments are isolated on a solid phase to provide first and second isolated affinity-labeled peptide fragments. The first and second isolated peptide fragments are released from the solid phase to provide first and second released peptide fragments. The first and second released peptide fragments are then reacted with an isotope-coded agent to provide first and second isotope-coded peptide fragments. The first released peptide fragments are reacted with a first agent that includes one or more stable isotopes. The second released peptide fragments are reacted with a second agent that includes no stable isotopes or fewer stable isotopes than the first agent. The first and second isotope-coded peptide fragments are then analyzed. In one embodiment, the first and second isotope-coded peptide fragments are combined and then analyzed by mass spectrometry. The mass spectral analysis of the first and second isotope-coded peptide fragments provide quantitative information relating to the difference in the amounts (e.g., expression levels) of the proteins in the first and second protein mixtures.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 compares mass chromatograms of m/z 655.4, which corresponds to the quadruply-charged ion, $(M+H_4)^{+4}$, of the peptide VIHDHFGIVEGLMTTVHAITATQK from G3P_RABIT, derived from a representative method of the invention (top chromatogram, labeled ICRAP) and a representative isotope coded affinity tag method (bottom chromatogram, labeled ICAT). Three other non-cysteine containing peptides were found in the ICAT preparation that produced a sufficiently intense ion to trigger MS/MS data acquisition—NVLQPSSVDSQTAMVLVNAIVFK and ILELPFASGTMSMLVLLPDEVSGLEQLESIINFEK from OVAL_CHICK, and VAGTWYSLAMAASDISLL-DAQSAPLR from LACB_BOVIN. These peptides were not found in the preparation derived from the method of the invention.

DETAILED DESCRIPTION OF THE INVENTION

Figure 1:
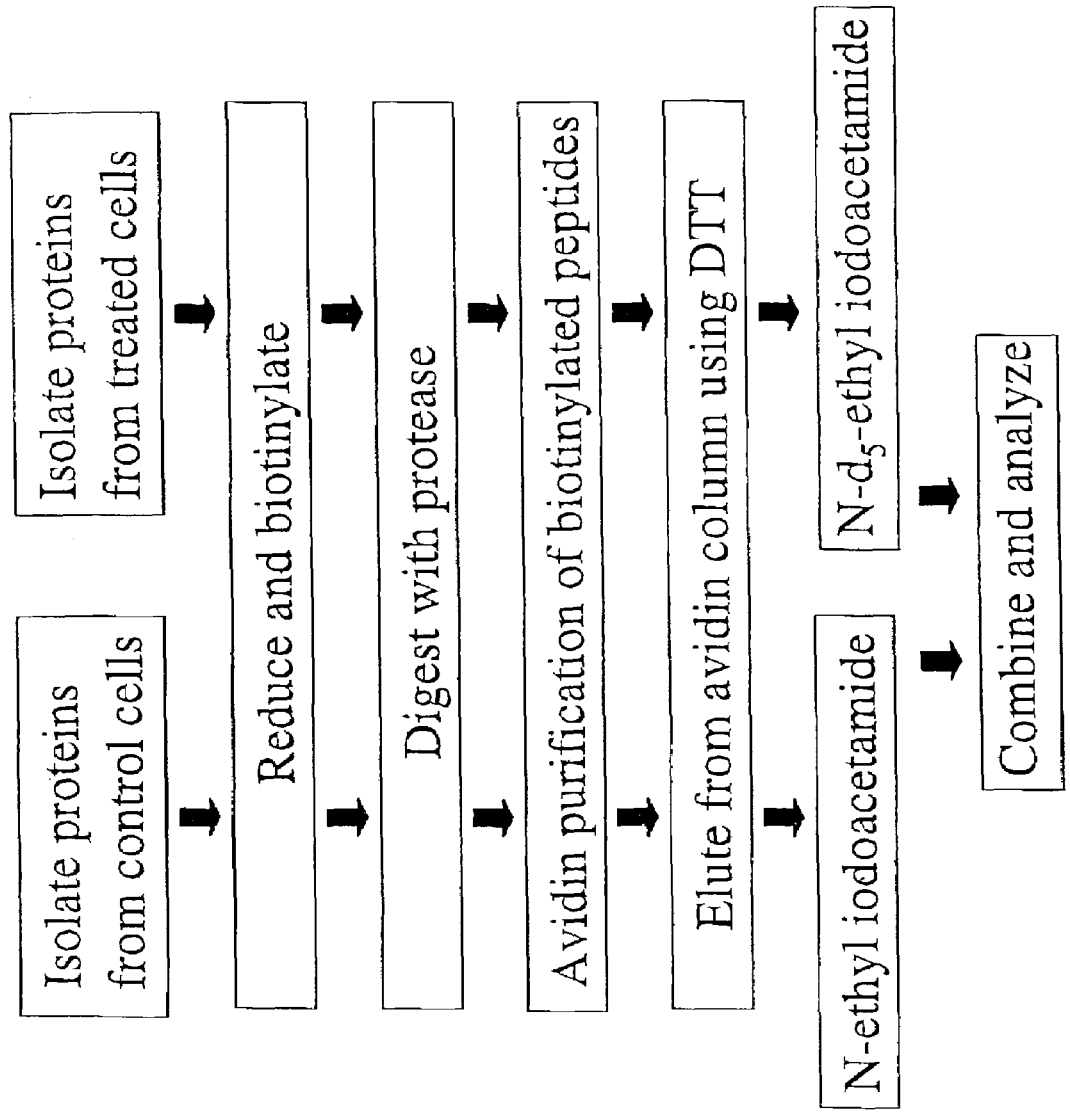
FIG. 1 is a flow diagram illustrating a representative method of the invention. Sample proteins are reduced and biotinylated with a reagent that has a reducible linker. Next the samples are digested with a protease such as trypsin. The biotinylated peptides are isolated using avidin beads, and eluted with a reducing reagent. The thiols on the cysteines are then alkylated with either a light reagent (N-ethyl iodoacetamide) or a heavy reagent (N-$d_5$-ethyl iodoacetamide), and then the two samples are mixed prior to any further HPLC fractionation or mass spectrometry.

In one aspect, the present invention provides a method for incorporating a stable isotope into a protein or peptide fragment. In the method, a protein or peptide fragment is reacted with an agent that includes one or more stable isotopes to provide an isotope-labeled protein or peptide fragment.

In the method, a stable isotope is incorporated into the protein or peptide fragment through the reaction of an amino acid residue of the protein or peptide fragment with an agent that includes one or more stable isotopes. Suitable amino acid residues include any residue capable of coupling with the isotope-labeled agent and include cysteine, lysine, hydroxylysine, serine, threonine, hydroxyproline, asparagine, methionine, arginine, histidine, tryptophan, phenylalanine, tyrosine, aspartic acid, and glutamic acid. Suitable agents include those capable of coupling with an amino acid residue such as, for example, alkylating agents and acylating agents. In one embodiment, the isotope-labeled protein or peptide fragment is a cysteine-containing protein or peptide fragment that is labeled through the protein's or peptide fragment's cysteinyl residue sulfhydryl group. The peptide fragment can be obtained from proteolytic digestion of a protein.

In one embodiment of the method, the protein or peptide fragment for reaction with the isotope-labeled agent is obtained by reacting a cysteinyl residue in a protein or peptide fragment with an affinity reagent; isolating the affinity-labeled protein or peptide fragment on a solid phase; and releasing the isolated protein or peptide fragment from the solid phase. The cysteinyl residue for reaction with the agent can be made available by reducing a protein or peptide fragment.

As used herein, the term "affinity reagent" refers to a reagent that introduces one member of a specific binding pair into the protein or peptide fragment such that the resulting protein or peptide fragment, referred herein to as an "affinity-labeled" protein or peptide fragment, can be captured and isolated by a solid phase bearing the other member of the specific binding pair. Suitable specific binding pairs are known and include, for example, sugar ligand and lectin, hapten/antigenic determinant ligand and antibody, Fc ligand and protein A, nucleic acid and complementary nucleic acid oligomer, polymer, or analog, among others. In one embodiment, the specific binding pair is a biotin/avidin system. In such a system, the affinity reagent is a biotinylation reagent, the affinity-labeled protein or peptide fragment is a biotinylated protein or peptide fragment, and the solid phase is an avidin solid phase.

A biotinylation reagent useful in the method of the invention includes a biotin moiety covalently attached to a protein reactive moiety such that the protein reactive moiety when coupled to protein provides a cleavable linkage intermediate the biotin moiety and protein reactive moiety. Cleavage of the linkage facilitates the release of the protein or peptide fragment from the solid phase. In one embodiment, the cleavable linkage is a disulfide linkage.

The reagent's biotin moiety can be any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone. In one embodiment, the biotin moiety is biotin.

The reagent's protein reactive moiety is a functional group that is reactive with a protein residue's functional group. The reagent's protein reactive moiety can be reactive toward a variety of functional groups including, for example, a sulfhydryl group (cysteine), an amino group (lysine), a hydroxy group (serine), and a carboxy group (glutamic acid). In one embodiment, the reactive moiety is reactive toward a sulfhydryl group. Suitable protein reactive functional groups include acylating groups (e.g., carboxylic acids and their reactive derivatives) and alkylating groups (e.g., ($\alpha$-halo carboxylic acids and their derivatives), among others In one embodiment, the protein reactive moiety is a pyridyldithiol moiety.

In one embodiment, the biotinylation reagent is N-[6-(biotinamido)hexyl]-3'-(2'-pyridyldithio)propionamide, Biotin-HPDP, commercially available from Pierce Chemical Co., Rockville, Ill.

As noted above, in one embodiment of the method, the affinity-labeled protein or peptide fragment is isolated on a solid phase. Suitable solid phases include any solid phase capable of capturing the affinity-labeled protein or peptide fragment. The solid phase bears the complement member of the binding pair. For biotinylated proteins and peptide fragments, the solid phase is an avidin solid phase. As used herein, the term "avidin" refers to any biotin-binding protein other than an immunoglobulin that binds biotin including both natural proteins and recombinant and genetically engineered proteins. The term includes the two common biotin-binding proteins known as "egg white or avian avidin" and "streptavidin." Egg white or avian avidin, commonly referred to simply as avidin, is a protein that is a constituent of egg white and forms a noncovalent complex with biotin. Streptavidin is a protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin and crosslinked avidin.

In one embodiment of the method, the protein or peptide fragment for reaction with the isotope-labeled agent is ultimately obtained by releasing the isolated protein or peptide fragment from the solid phase. In one embodiment the protein or peptide fragment is released from the solid phase by cleaving the cleavable linkage, for example, a disulfide linkage, incorporated into the protein or peptide fragment on reaction with the affinity reagent. Release from the solid phase provides a protein or peptide fragment having a sulfhydryl group that is reactive toward the isotope-labeled agent. In one embodiment, the released protein or peptide fragment is the same as the protein or peptide fragment reacted with the affinity reagent.

The stable isotope is incorporated into the released protein or peptide fragment by reaction with an isotope-labeled agent. The released protein or peptide fragment can be alkylated with an alkylating agent that includes one or more stable isotopes. In one embodiment the isotope-labeled agent is N-ethyl-$d_5$-iodoacetamide. N-Ethyl-$d_5$-iodoacetamide can be prepared as described in Example 1. In another embodiment the isotope-labeled agent is acrylamide-$d_3$ ($CD_2$=CD—C(=O)—$NH_2$).

Generally, suitable isotope-labeled agents include any agent capable of forming a covalent bond to sulfur and bearing one or more stable isotopes. Because the proteins and peptide fragments are ultimately analyzed by mass spectrometry, preferred isotope-labeled agents include two or more stable isotopes. In one embodiment the agent includes at least two stable isotopes. In another embodiment the agent includes at least three stable isotopes. In a further embodiment the agent includes at least four stable isotopes. In another embodiment the agent includes at least five stable isotopes.

Stable isotopes useful in the method include carbon (i.e., $^{13}C$) and hydrogen (i.e., $^{2}H$, deuterium) stable isotopes.

In another aspect of the invention, methods for incorporating a stable isotope into a protein or peptide fragment and methods for measuring protein levels in two or more protein or peptide fragment mixtures are provided. The method for measuring protein levels in two or more protein mixtures includes incorporating a stable isotope into the protein or peptide fragment.

In one method, the cysteinyl residues of proteins in first and second protein mixtures are reacted with an affinity reagent to provide first and second affinity-labeled protein mixtures. Suitable affinity reagents include those described above. The cysteinyl residues can be made available by first treating the protein mixtures with a reducing agent. The first and second affinity-labeled proteins are isolated on a solid phase to provide first and second isolated affinity-labeled proteins. The first and second isolated proteins are released from the solid phase to provide first and second released proteins. Release from the solid phase can be through cleavage of a cleavable linkage incorporated into the protein or peptide fragment on reaction with the affinity reagent. In one embodiment, the released proteins include sulfhydryl groups. The first and second released proteins are then reacted with an isotope-labeled agent (e.g., a sulfhydryl alkylating agent) to provide first and second isotope-coded proteins. Suitable isotope-labeled agents include those described above. The first released proteins are reacted with a first agent that includes one or more stable isotopes (e.g., N-ethyl-d$_5$ iodoacetamide). The second released proteins are reacted with a second agent that includes no stable isotopes or fewer stable isotopes than the first agent (e.g., N-ethyl iodoacetamide). The first and second isotope-coded proteins can then analyzed. In one embodiment, the first and second isotope-coded proteins are combined prior to analysis. The isotope-coded proteins can be analyzed by mass spectrometry. The mass spectral analysis of the first and second isotope-coded proteins provide quantitative information relating to the difference in the amounts (e.g., expression levels) of the proteins in the first and second protein mixtures.

In another method, isotope-coded peptide fragments are prepared and then analyzed. In the method, the cysteinyl residues of proteins in first and second protein mixtures are reacted with an affinity reagent to provide first and second affinity-labeled protein mixtures. Suitable affinity reagents include those described above. The cysteinyl residues can be made available by first treating the protein mixtures with a reducing agent. The first and second affinity-labeled protein mixtures are then digested to provide first and second peptide fragment mixtures, the fragments including first and second affinity-labeled peptide fragments. The first and second affinity-labeled peptide fragments are isolated on a solid phase to provide first and second isolated affinity-labeled peptide fragments. The first and second isolated proteins are released from the solid phase to provide first and second released peptide fragments. Release from the solid phase can be through cleavage of a cleavable linkage incorporated into the peptide fragment on reaction with the affinity reagent. In one embodiment, the released peptide fragments include sulfhydryl groups. The first and second released peptide fragments are then reacted with an isotope-labeled agent (e.g., a sulfhydryl alkylating agent) to provide first and second isotope-coded peptide fragments. Suitable isotope-labeled agents include those described above. The first released peptide fragments are reacted with a first agent that includes one or more stable isotopes (e.g., N-ethyl-d$_5$ iodoacetamide). The second released peptide fragments are reacted with a second agent that includes no stable isotopes or fewer stable isotopes than the first agent (e.g., N-ethyl iodoacetamide). The first and second isotope-coded peptide fragments can then analyzed. In one embodiment, the first and second isotope-coded peptide fragments are combined prior to analysis to provide an isotope-coded peptide fragment mixture. The peptide fragment mixture can be analyzed by mass spectrometry. The mass spectral analysis of the first and second isotope-coded peptide fragments provide quantitative information relating to the difference in the amounts (e.g., expression levels) of the proteins in the first and second protein mixtures.

It will be-appreciated that the method of the invention includes measuring protein levels in two or more protein mixtures. The number of protein mixtures that can be analyzed by the method will depend on the complexity of the protein mixtures and the nature of the isotope-labeled agents. The greater the number of protein mixtures, the greater the number of distinct isotope-labeled agent required for the analysis. Each protein mixture merely requires a distinct isotope-labeled agent. Accordingly, the method of the invention is not limited to comparing protein levels in two protein mixtures, but is applicable to determining the protein levels in a plurality of protein mixtures.

In another embodiment of the method, the protein or peptide fragment for reaction with the isotope-labeled agent is obtained from a thiol-containing residue in a protein or peptide fragment. The thiol-containing residue can be formed by a variety of methods. For example, the thiol-containing residue can be obtained by isolating a tryptophan-containing protein or peptide fragment on a solid phase that provides a thiol-modified tryptophan residue on the release of the protein or peptide fragment from the solid phase. A suitable solid phase is a chlorodithiol (i.e., —S—S—Cl) solid phase that is reactive toward tryptophan residues. A suitable chlorodithiol solid phase is commercially available under the designation Pi$^3$ Tryptophan Reagent from The Nest Group, Inc., Southborough, Mass. Release of the isolated tryptophan-containing protein or peptide fragment from the solid phase provides the thiol-modified tryptophan protein or peptide fragment, which can be labeled with the isotope-labeled agent to provide an isotope coded-protein or peptide fragment.

In another embodiment, the thiol-containing residue is a gamma-S labeled residue incorporated into a protein or peptide fragment through phosphorylation with ATP-gamma-S. The gamma-S modified protein or peptide fragment includes an available thiol group that can be reacted with the isotope-labeled agent to provide an isotope coded-protein or peptide fragment.

Thus, in another aspects, the invention provides a method for incorporating a stable isotope into a tryptophan-containing protein or peptide fragment, and a method for incorporating a stable isotope into a protein or peptide fragment that has been phosphorylated to provide an available thiol group. The isotope-coded tryptophan-containing protein or peptide fragment can be used to measure the amount of tryptophan-containing proteins or peptide fragments in mixtures as described above. Similarly, the isotope-coded phosphorylated protein or peptide fragment having an available thiol group can be used to measure the amount of phosphorylation in protein or peptide fragment mixtures as described above.

A representative method of the invention is schematically illustrated in FIG. 1. Referring to FIG. 1, in the representative method, sample proteins (e.g., isolated proteins from control cells and isolated proteins from treated cells) are reduced to provide available sulfhydryl groups which are then biotinylated with a reagent that having a reducible linker. Next the samples are digested with a protease such as trypsin. The biotinylated peptides are then isolated using avidin beads, and eluted from the avidin with a reducing reagent. The thiols on the cysteines are then alkylated with either a light reagent (e.g., N-ethyl iodoacetamide) or a heavy reagent (e.g., N-$d_5$-ethyl iodoacetamide), and then the two samples are mixed prior to any further HPLC fractionation or mass spectrometry.

The method includes isotopic coded labeling of peptide fragments originating from proteins in each mixture and mass spectral analysis of the isotope-labeled peptide fragments to obtain quantitative information relating to the level of expression of the proteins in each mixture.

For illustration purposes, a representative embodiment of a method of the invention using a biotinylation reagent as an affinity reagent follows.

In the method, the cysteinyl residues of proteins in first and second protein mixtures are reacted with a biotinylation reagent to provide first and second biotinylated protein mixtures. The biotinylation reagent includes a biotin moiety attached to a protein reactive moiety through a cleavage disulfide linkage. Prior to biotinylation, the proteins in the mixtures can be treated with a reducing agent to make available sulfhydryl groups.

After biotinylation, the first and second protein mixtures are digested to provide first and second peptide fragments. The biotinylated fragments include peptide fragments containing cysteinyl residues that are biotinylated.

The first and second biotinylated peptide fragments are isolated by avidin affinity chromatography to provide first and second isolated biotinylated peptide fragments. Through their biotinylation, the peptide fragments can be isolated from other peptide fragments that do not include biotin, thereby selectively reducing the number of peptide fragments for analysis.

After capture on a solid phase, the first and second isolated peptide fragments are treated with a reducing agent to cleave the disulfide linkage covalently linking the peptide fragment to the captured biotin moiety resulting in the release of the isolated peptide fragments from avidin. Suitable reducing agents include disulfide reducing agents such as dithiothreitol (DTT).

The use of a biotinylation reagent that provides a disulfide linkage between the biotin moiety and the peptide fragment results in a highly selective and gentle elution of the isolated peptide fragment from the avidin solid phase. The advantage of this is that the non-specifically bound peptides will not be released, and will remain bound to the avidin beads, thereby resulting in a cleaner preparation of cysteine-containing peptides. Furthermore, reductive cleavage of the disulfide linkage provides the released peptide fragment with a sulfhydryl group.

To distinguish between the peptide fragments originating from the first and second protein mixtures, the first and second released peptide fragments are reacted with an isotope-coded alkylating agent to provide first and second isotope-coded peptide fragments. The first released peptide fragments are alkylated with a first alkylating agent that includes one or more stable isotopes, and the second released peptide fragments are alkylated with a second alkylating agent that includes no stable isotopes or fewer stable isotopes than the first alkylating agent.

In one embodiment the first alkylating agent is N-ethyl-$d_5$ iodoacetamide, and the second alkylating agent is N-ethyl iodoacetamide. N-ethyl-$d_5$-iodoacetamide can be prepared as described in Example 1. Briefly, reaction of ethyl amine with 1,1'-diiodoacetic anhydride provides ethyl iodoacetamide. Similar reaction with $d_5$-ethylamine provides N-ethyl-$d_5$ iodoacetamide. By selection of the amine and stable isotope labeled amine, a variety of suitable isotope-coded alkylating agents can be prepared.

In another embodiment, the first alkylating agent is acrylamide-$d_3$ ($CD_2$=CD—C(=O)—$NH_2$), and the second alkylating agent is acrylamide. Both of these alkylating agent are commercially available. For larger peptides, the three mass unit difference obtained by alkylating with acrylamide/$d_3$-acrylamide is less desirable as the interpretation of mass spectra obtained for these fragments can be complicated by the fragments' $^{13}C$ isotopic clusters.

Generally, suitable isotope coded alkylating agents include any alkylating agent capable of forming a covalent bond to sulfur and bearing one or more stable isotopes. Because the peptide fragments are ultimately analyzed by mass spectrometry, preferred first and second isotope coded alkylating agents have molecular weights that differ by at least two, more preferably at least three, and even more preferably at least five mass units.

Stable isotopes include carbon (i.e., $^{13}C$) and hydrogen (i.e., $^{2}H$, deuterium) stable isotopes.

In the representative method, the first and second isotope-coded peptide fragments are then combined and further analyzed by mass spectrometry. The mass spectral analysis of the combined first and second isotope coded peptide fragments provide information relating to the difference in the amounts (e.g., expression levels) of the proteins in the first and second protein mixtures.

To test the yields of the method of the invention, two equal aliquots of bovine serum albumin (BSA) were prepared. For one of the aliquots, the protein was reduced, labeled with HPDP-biotin, biotinylated peptides were isolated on monoavidin beads, eluted with DTT, and alkylated with N-ethyl iodoacetamide (the light reagent). The other aliquot of BSA was reduced and alkylated with N-ethyl-$d_5$-iodoacetamide without going through the biotinylation and monoavidin procedures. The two samples were mixed and analyzed by MALDI-TOF mass spectrometry, where it was found that the biotinylation and avidin purification steps had an overall yield of approximately 75%. The yield of the alkylation step was estimated to be greater than 95% by first alkylating a sample of BSA with the light reagent, followed by a thiol quench and the addition of an excess of the heavy reagent. No alkylation by the heavy reagent was observed. Thus, the overall yield of this procedure is conservatively estimated to be in excess of 70%.

A representative method of the invention providing relative quantitative protein measurements is described in Example 2. A representative method for providing relative quantitative protein measurements by an isotope coded affinity tag (ICAT) method is described in Example 3. The ability of the two methods to provide relative quantitative measurements was tested using two mixtures of protein standards in which proteins in the two mixtures differed in their amounts. The results are summarized below in Table 1. In Table 1, the ratio of heavy/light label for the method of the invention is provided under the heading referred to as ICRAP (for "isotope coded reducible affinity proteomics")

and the ratio for the isotope coded affinity tag method is provided under the heading referred to as ICAT (for "isotope coded affinity tag").

ICAT-labeled peptide that is completely up or down regulated. The distinction can only be made by tandem mass spectrometric sequencing. In the data analysis of the ICAT

TABLE 1

Comparison of Quantitative Results of Protein Standard Mix.

| Protein | Peptide | Expected | CAT | ICRAP |
|---|---|---|---|---|
| LCA_BOVIN | ALCSEK | 1.0 | .23 | — |
| | LDQWLCEK | 1.0 | .87 | 0.88 |
| | FLDDDLTDDIMCVK | | .87 | 0.87 |
| | DDQNPHSSNICNISCDK | | .0 | |
| OVAL_CHICK | YPILPEYLQCVK | 0.5 | .65 | 0.62 |
| | GSIGAASMEFCFDVFK | | .88 | 0.47 |
| | VHHNANENIFYCPIAIMSALAMVYLGAK | | | 0.41 |
| | ADHPFLFCIK | | | 0.47 |
| PHS2_RABIT | WLVLCNPGLAEIIAER | 3.3 | .27 | 2.65 |
| | ICGGWQMEEADDWLR | | .17 | 2.66 |
| | LAACFLDSMATLGLAAYGYGIR | | .46 | 2.64 |
| | TCAYTNHTVLPEALER | 3.3 | .09 | 2.73 |
| LACB_BOVIN | WENDECAQK | 0.25 | | 0.28 |
| | LSFNPTQLEEQCHI | | | 0.41 |
| | YLLFCMENSAEPEQSLACQCLVR | | | 0.44 |
| G3P_RABIT | VPTPNVSSVVDLTCR | 2.0 | | 2.8 |
| | IVSNASCTTNCLAPLAK | 2.0 | .84 | 2.03 |

Referring to Table 1, it was found that in some cases the observed ratios not only deviated from what was expected, but also that there was some scatter in ratios measured for peptides from the same protein. Some of the scatter could be due to the fact that ratios derived from lower intensity ions are likely to have a higher degree of error.

Figure 2:
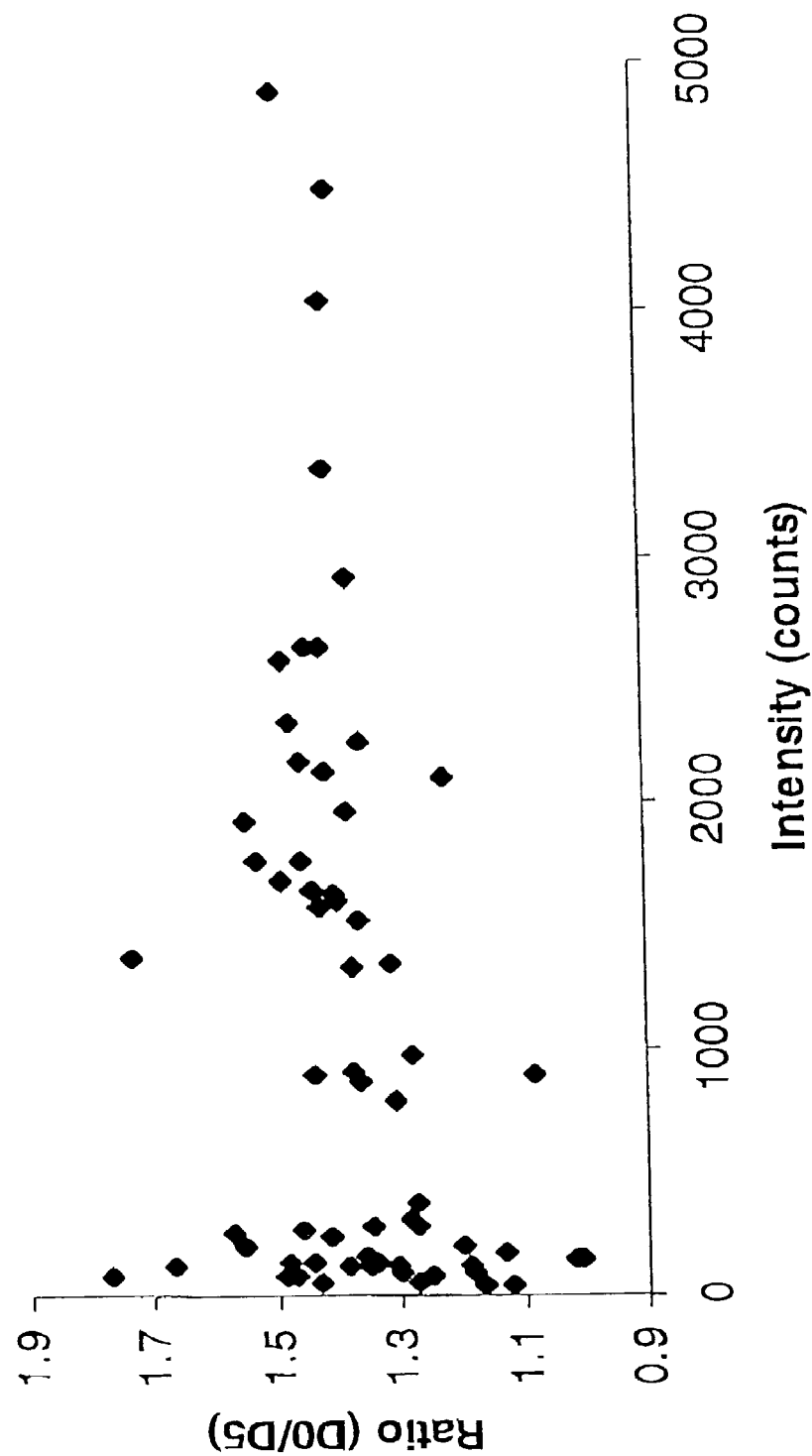
FIG. 2 is a graph plotting the ratio (D0/D5) versus intensity (counts) illustrating increasing error with decreasing ion intensity. Bovine serum albumin was labeled 1:1 with N-ethyl and N-$d_5$-ethyl iodoacetamide, digested with trypsin, and analyzed four times by LC/MS. The ratio of N-ethyl versus N-$d_5$-ethyl iodoacetamide labeling (D0)/D5) for various ions is plotted against ion intensity.

To establish the degree to which ion intensity affects errors in the ion intensity ratios, a mixture of BSA labeled 1:1 with N-ethyl iodoacetamide and N-ethyl-$d_5$ iodoacetamide was digested with trypsin and varying amounts were repeatedly analyzed by LC/MS. The observed ratio of light reagent labeling to heavy turned out to be closer to 1.4 and, as expected, there was greater variation in the measured ratios as the ion intensity dropped (see FIG. 2). For the given instrument settings at the time of data acquisition, the estimation of errors for ions with counts less than 200 (95% confidence limit) were estimated to be +/−30%. For ions present at counts between 200 to 1500, 1500 to 3000, and 3000 to 5000, the estimated errors dropped off with increasing intensity: +/−20%, 10%, and 5%, respectively. Estimation of the anticipated errors in the measurement of intensity ratios is of critical importance when trying to determine if minor changes in protein abundance are real. Given that the relationship between ratio error and ion intensity (see FIG. 2) depends on the instrument, as well as the instrument settings, a determination of this relationship would have to be established from time to time. Other causes for the variations in labeling of peptides derived from the same protein could be due to variability in the alkylation efficiencies, perhaps as a result of steric hindrance.

In one embodiment, the method of the invention includes the use of a biotinylation reagent having a cleavable linkage. One of the advantages of using a cleavable biotinylation linker is that rather than eluting biotinylated peptides with acidic pH, which is just as likely to release non-specifically bound peptides, a gentler elution can be performed using reducing agents such as DTT. The significance of this is that non-cysteine containing peptides that bind monoavidin will appear as a single mass spectrometric peak without the presence of a heavy or light ICAT-labeled partner. The presence of such ions could easily be confused as being an experiments of the protein standard mixtures, a database search of the MS/MS spectra revealed the presence of four peptides that were identified but did not contain cysteine, and therefore could not be ICAT labeled (e.g., FIG. 3). None of these peptides were found in the data set obtained by the method of the invention. By reducing the level of non-specifically bound peptides, in data dependent LC/MS/MS mode the mass spectrometer will spend less time sequencing unlabeled uninteresting peptides.

Figure 4:
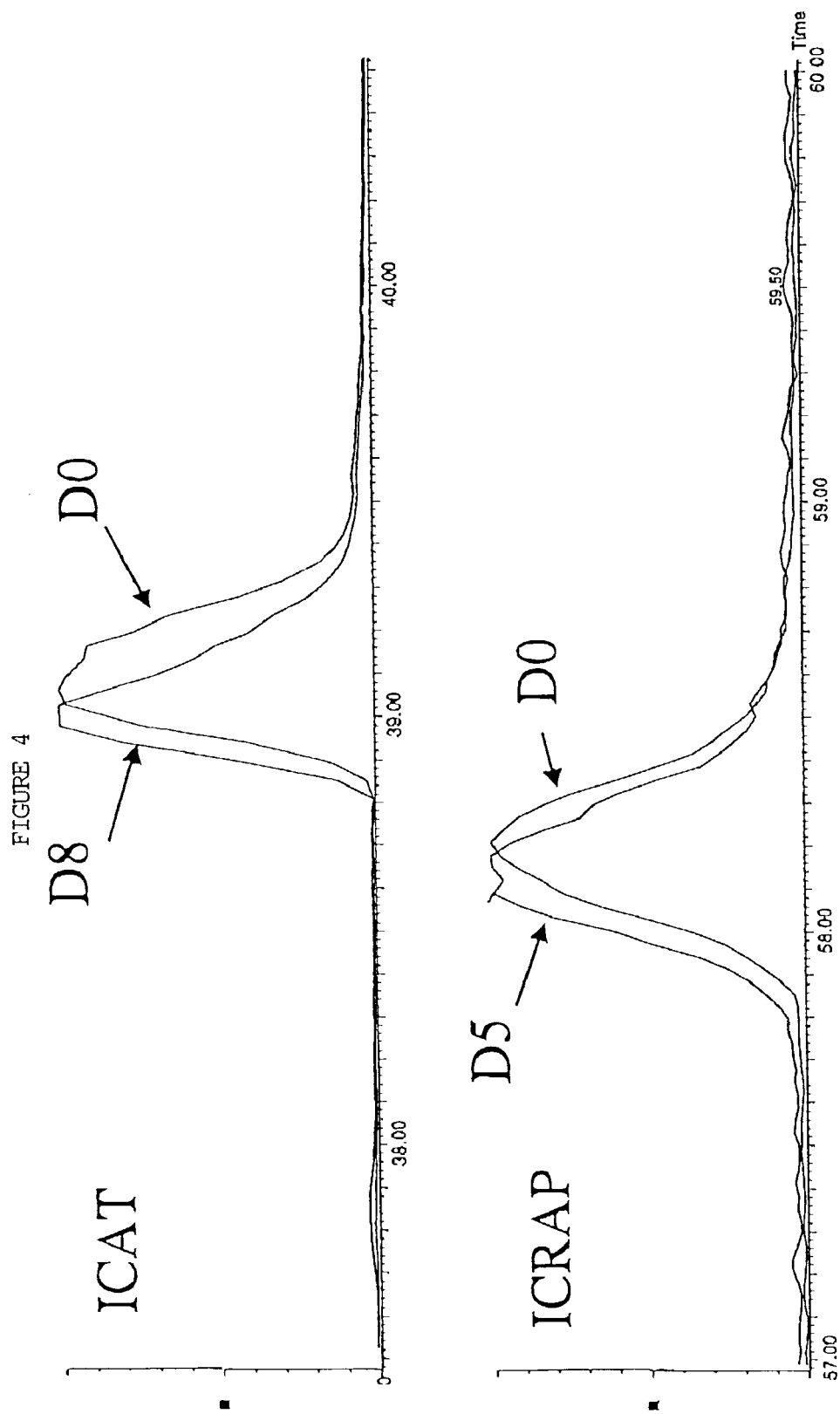
FIG. 4 compares mass chromatograms of heavy and light isotope labeled peptide, LAACFLDSMATLGLAAYGY-GIR, from phosphorylase. The heavy isotope labeled peptide always elutes before the light isotope labeled peptide. However, for labeling with an isotope coded affinity tag method (labeled ICAT), where the heavy isotope labeling incorporates eight deuterium atoms, the difference in elution times is greater than for a representative method of the invention (labeled ICRAP) where the heavy isotope label has five deuterium atoms.

Another distinction between the method of the invention and the isotope coded affinity tag (ICAT) method was the observation that peptides labeled with the heavy and light versions had greater separations for ICAT labeled peptides. The heavy ICAT reagent contains eight deuterium atoms, whereas the heavy reagent in the method of the invention has five deuterium atoms. A difference of 5 mass units between the heavy and light labeled peptides obtained by the method of the invention is sufficient in most cases to allow a clear distinction between $^{13}C$ isotope clusters, yet will not result in as much of a chromatographic separation as observed in ICAT labeled peptides (see FIG. 4). The significance of this is that one has to be a bit more careful when trying to quantitate if the two isotopically labeled forms of the same peptide elute differently. Although labeled peptides obtained by the method of the invention tend to co-elute to a greater extent than ICAT labeled peptides, in practice, for both of these methods it is necessary to perform both LC/MS and LC/MS/MS experiments. The former is for obtaining good quantitative measurements, and the latter is for peptide identification.

Figure 5:
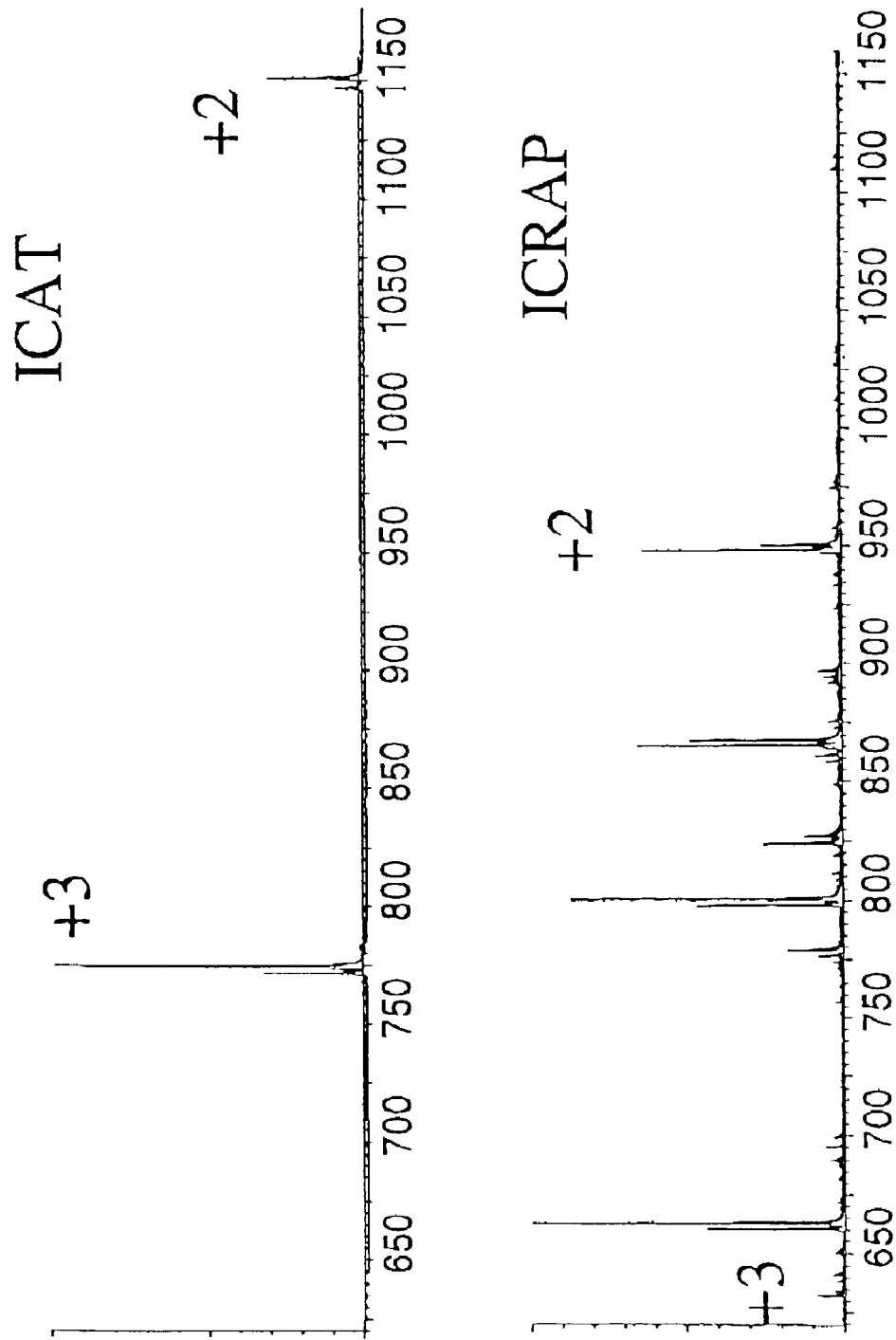
FIG. 5 compares the mass spectrum of peptide ions derived from an isotope coded affinity tag method (top panel, labeled ICAT) with the mass spectrum of peptide ions derived from the method of the invention (bottom panel, labeled ICRAP) for ICGGWQMEEADDWLR. The ICAT method promotes the formation of higher charge states compared to labeling in accordance with the present invention.
Figure 6:
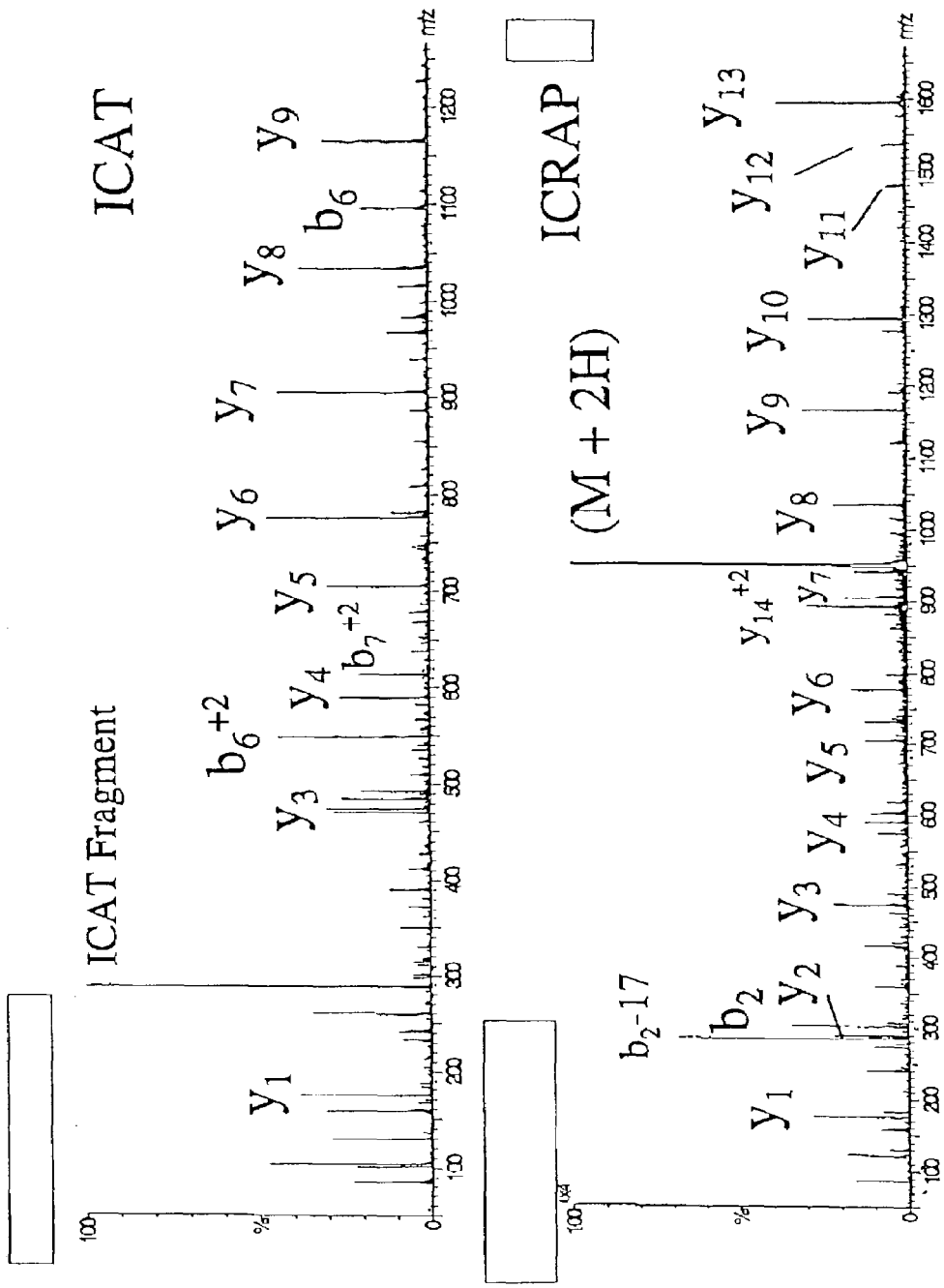
FIG. 6 compares the MS/MS spectrum of m/z 753.7, the triply charged ion for ICGGWQMEEADDWLR obtained from an isotope coded affinity tag method (top panel, labeled ICAT, labeled with the D8 ICAT reagent) with the MS/MS spectrum of the doubly charged ion at m/z 947.4 from the same peptide obtained from a representative method of the invention (bottom panel, labeled ICRAP, labeled with a D0 reagent). The most abundant ion in the top panel is a fragment derived from the ICAT adduct. All sequence-specific fragment ions have been labeled as b- or y-type ions (**). Note that the spectrum of the doubly charged peptide obtained by the method of the invention exhibits a complete series of y-type ions, whereas the spectrum of the triply charged peptide obtained by the ICAT method is incomplete. This is partly due to the selection of a triply charged ion as the precursor for the ICAT spectrum.

Another concern with the ICAT reagent is that it adds approximately 450 mass units for each cysteine present in any given peptide, which can result in a substantial increase in mass for peptides with more than one cysteine. Furthermore, the addition of the ICAT reagent tends to increase the charge state for many peptides (see FIG. 5). The MS/MS spectra of doubly charged precursor ions generally provide a fragmentation pattern that gives more complete coverage of the sequence, as compared to that produced by triply-charged precursors (see FIG. 6). In comparison, labeled peptides obtained from the method of the invention add only 90 mass units per cysteine, and there is no increase in peptide charge states (see FIG. 5), which will usually result in a more favorable fragmentation pattern (see FIG. 6). Also, ICAT labeling introduces a number of functional groups that can be sites of labile fragmentation, which results in MS/MS spectra having ICAT-specific fragment ions, in addition to the sequence-specific peptide fragment ions. ICAT fragments and losses of ICAT from precursors and sequence-specific fragment ions can be observed. The ions at m/z 284 (from the light ICAT reagent) and m/z 288 are often the most prominent ions in ICAT-labeled peptide MS/MS spectra (see FIG. 6). Because there is only a limited amount of precursor ion current available for producing fragment ions, shunting a significant portion of this current into the production of uninformative fragment ions can limit the sensitivity. In contrast, labeling obtained by the method of the invention is not significantly different from the standard iodoacetamide alkylation of cysteine, which is a modification that is relatively stable upon collisional activation.

One difference between the method of the invention and the ICAT method is that in the method of the invention the isotopically labeled peptides are not mixed together until late in the procedure. This adds to the amount of work required in that two samples are separately digested with trypsin, biotinylated, isolated on avidin, released and labeled prior to mixing. In contrast, the ICAT procedure introduces the isotopic labeling early in the experiment, and then the combined samples are worked up as a single mixture. It might be argued that working up two separate samples and mixing late in the procedure is more likely to introduce artifacts, where proteins might appear to be up or down regulated, but, in fact, additional protein losses were suffered for one of the two samples. In general, this will not be a problem if two conditions can be met: (1) differential losses suffered in the separate work ups are non-specific; and (2) most proteins in the mixture are not up or down regulated. Condition number one seems reasonable; for example, it is unlikely that slightly different avidin yields or protein precipitation recoveries will be selective for specific proteins. If the second condition is met, then one could establish a ratio that represents no change in relative protein amounts. For example, if one of the samples suffered more overall protein losses in one of the precipitation steps compared to the second samples, then instead of observing a ratio of 1:1 for a protein that did not change its relative amounts, one might observe a ratio of 1:1.2. Basically, the data analysis would be to plot out a histogram of the different ratios, assume that the most common ratio represents no change in relative amounts, and then establish confidence intervals beyond which are cases where the proteins did change. In short, separate work ups for two samples is not all that likely to result in artifacts, although it is a bit more work. One additional disadvantage should be mentioned, which is that the HPDP-biotin reagent has only limited solubility. The maximum concentration of this reagent is 2 mM if a 4 mM stock solution in DMSO is diluted 1:1 with the sample. In order to obtain a sufficient molar excess of the reagent over cysteine thiols, either one may be limited in the total amount of protein that can be analyzed, or the volume of the reaction needs to be increased.

The present invention provides an advantageous method for making relative quantitative measurements of proteins in mixtures. In one embodiment of the method, cysteine-containing peptides are isolated via avidin beads using biotinylation reagent that includes a spacer arm that can be cleaved using reducing agents. The biotinylation reagent can be a commercially available reagent. The stable isotope labeling is accomplished by alkylating the released cysteine thiols using reagents (e.g., N-ethyl iodoacetamide and N-$d_5$-ethyl iodoacetamide) that can be synthesized in a single step using inexpensive reagents. The five mass unit difference between the two alkylating agents is sufficient to avoid contributions of ion intensity from the naturally occurring $^{13}C$ isotope peaks, yet minimizes the differences in reversed phase HPLC retention time for identical peptides labeled with the two reagents. The advantage of using a biotinylation reagent with a cleavable linker is that it reduces the possibility of observing unlabeled peptides that may non-specifically bind to the avidin beads. In the method, peptides are gently eluted from avidin using reducing agents, which has the affect of minimizing non-specifically bound peptides (fewer non-specifically bound peptides, including those lacking cysteine, are observed). In addition, the labeling does not greatly increase the peptide mass and charge in electrospray ionization, which has beneficial effects on fragmentation characteristics upon low energy collision induced dissociation.

In comparison to the isotope coded affinity tag (ICAT) method, the change in peptide mass introduced by the method of the invention is minimal, which has a favorable impact on the fragmentation of the peptide in MS/MS. There is no increase in the number of charges on the peptide ions when labeled in accordance with the present method, whereas introduction of an ICAT label often increases the intensity of higher charge state ions. Whereas doubly charged precursor ions tend to provide fragmentations with more complete sequence coverage, ICAT labeled precursor ions typically have three or more charges. Furthermore, the most abundant ions in MS/MS spectra of ICAT labeled peptides tend to be ICAT related fragment ions, which are absent from peptides labeled using the method of the invention.

The following examples are provided for the purpose of illustrating, not limiting, the invention.

EXAMPLES

Example 1

Synthesis of Representative Isotope Coded Alkylating Reagents: N-(Ethyl-$d_5$) Iodoacetamide and N-Ethyl Iodoacetamide N-(Ethyl-$d_5$) Iodoacetamide. Ethyl-$d_5$-amine hydrochloride (0.85 g, 9.81 mmol) was suspended in a solution of iodoacetic anhydride (3.47 g, 9.81 mmol) in dichloromethane (40 mL) and cooled to 0° C. A solution of 3.6 mL, 20.6 mmol) of N,N-diisopropylethylamine in dichloromethane (10 mL) was added dropwise over 20 minutes. The reaction was stirred at 0° C. for 30 minutes then allowed to stir to room temperature for 4 hours. The solvent was evaporated to give a yellow syrup. The syrup was dissolved in ethyl acetate (100 mL) and washed with 1N hydrochloric acid (2×50 mL), then saturated sodium bicarbonate solution (2×50 mL), then saturated sodium chloride solution (50 mL). After drying over anhydrous magnesium sulfate, the organic solution was filtered and evaporated to give a light yellow solid. Purification by flash chromatography on silica gel (50 g) using 1:1 ethyl acetate/hexane for the elution gave the desired product as a white solid (446 mg, 21%). $^1H$ NMR: δ (chloroform-d), 6.04 (1H, br s), 3.68 ($^2H$, s). $^{13}C$ NMR: δ (chloroform-d), 166.6, 34.6, 13.3, -0.3. MS: 219 (M+H)+.

N-Ethyl Iodoacetamide. N-ethyl iodoacetamide was prepared from ethylamine hydrochloride in a manner analogous to that described above. $^1$H NMR: δ (chloroform-d), 6.37 (1H, br s), 3.67 ($^2$H, s), 3.28 ($^2$H, m), 1.13 (3H, t). $^{13}$C NMR: δ (chloroform-d), 166.9, 35.3, 14.3, -0.3. MS: 214 (M+H)+.

Example 2

Reversible Biotinylation of a Representative Protein Mixture

Preparation of a representative protein mixture. Protein standards were purchased from Sigma Chemical Co. (St. Louis, Mo.). Two protein mixtures were made containing hen ovalbumin (430 and 215 ug/ml), bovine beta-lactoglobulin (80 and 20 ug/ml), rabbit glyceraldehyde-3-phosphate dehydrogenase (49 and 98 ug/ml), rabbit phosphorylase b (97 and 323 ug/ml), and bovine alpha-lactalbumin (120 and 120 ug/ml).

Protein Reduction. Pelleted protein sample (25–200 ug) is solubilized in 100 ul of 8 M urea (stored over AG 501-X8 mixed bed resin to remove cyanate), 0.1 M TRIS pH 8.2, 1 mM EDTA, and heated at 100° C. for 5 minutes. The sample is cooled to room temperature and reduced using a final concentration of 5 mM tris(2-carboxyethyl)phosphine (TCEP) (Pierce Chemical Co., Rockford, Ill.). Nitrogen is blown over the sample and incubated for 10 minutes at 37° C. The excess reducing agent is removed using a chloroform/methanol/water extraction, and the resulting protein pellet was briefly dried using a vacuum centrifuge before immediately biotinylating.

Protein Biotinylation and Digestion. The dried pellet was solubilized in 50 ul of 8 M urea, followed by the addition of 50 ul of 0.1 M TRIS pH 8.2 containing 5 mM EDTA. The sample was incubated for 90 minutes in the dark under nitrogen following the addition of 100 ul of 4 mM biotin-HPDP (Pierce Chemical Co., Rockford, Ill.) stock solution in neat DMSO. The biotin-HPDP was removed using the chloroform/methanol/water extraction, and the pellet was dried briefly using a vacuum centrifuge before being resolubilized in 5 ul of 8 M urea. Next, 45 ul of 0.1 M TRIS pH 8.2 containing 1 mM EDTA was added to give a final urea concentration of 0.8 M before the addition of trypsin at an enzyme to substrate ratio of 1:50 by weight. Digestion proceeded overnight at 37° C. After digestion, the trypsin was partially destroyed by boiling for 20 minutes, followed by the addition of the trypsin inhibitor TLCK to a final concentration of 50 ug/ml, which was then incubated at 37° C. for 30 minutes. To avoid any residual tryptic activity, the pH was dropped to 5.2 by the addition of 2 ul of 3 M sodium acetate before mixing with the avidin beads.

Avidin purification of cysteine-containing peptides. Purification of biotinylated peptides was carried out using 50–200 ul of monoavidin beads for 50–200 ug total protein sample, and was performed batchwise in 1.5 ml eppendorf tubes. The monoavidin was washed twice using 5 bed volumes of PBS to remove preservatives, and then washed three more times using 5 bed volumes of 0.15 M sodium acetate, 0.15 M NaCl pH 5.2. The monoavidin beads were gently spun, and the supernatants removed. The reaction mixture was diluted in 0.15 M sodium acetate plus 1 mM EDTA and 0.15 M NaCl pH 5.2 to match the bed volume of monoavidin, and then combined with the avidin beads, and gently shaken on vortexer for 20 minutes at room temperature. The monoavidin beads were gently centrifuged, and the unbound supernatant was removed and saved. The monoavidin beads were washed three times in the sodium acetate pH 5 buffer and then two more times in 0.1 M TRIS pH 8.2. After the final wash, the monoavidin beads were suspended in 1 bed volume of 0.1 M TRIS pH 8.2 containing 1 mM EDTA, and dithiothreitol (DTT) was added to give a final concentration of 5 mM. The beads were gently agitated and incubated at 37° C. for 30 minutes. The samples were gently spun, and the supernatants set aside. Another bed volume of 0.1 M TRIS pH 8.2 containing 5 mm DTT and 1 mM EDTA was added to the monoavidin beads, mixed gently, centrifuged, and the supernatants removed. The two supernatants were pooled and partially vacuum centrifuged to reduce the volume to approximately 10 ul.

Alkylation of the purified cysteine-containing peptides. Alkylation of the purified cysteine-containing peptides was performed by resuspending the avidin eluates in 50 ul 8M urea followed by the addition of 50 ul of 0.1M TRIS pH 8.2. To reduce the possibility of the formation of mixed disulfides, an additional 5 mM DTT was added, and the samples were incubated at 55° C. for 20 minutes under nitrogen. The samples were cooled to room temperature and alkylating agent (either N-ethyl iodoacetamide or N-$d_5$-ethyl iodoacetamide) was added to give a final concentration of 30 mM of the alkylating reagent. Samples were incubated under nitrogen in the dark for 30 minutes. At this point, samples labeled with different isotopes can be mixed and analyzed.

Example 3

Representative Isotope Coded Affinity Tag (ICAT) Method

ICAT reagents were supplied by Applied Biosystems Inc. (Framingham, Mass.). Dried protein (50 ug, as described above) was solubilized in 100 ul 50 mM TRIS pH 8.5 plus 0.1% SDS, and boiled for five minutes. The denatured proteins were reduced by the addition of 1 ul 1 M TCEP for 10 minutes at 37° C. Reducing agent was removed by overnight acetone precipitation at −20° C. The pellet was suspended in 100 ul TRIS/SDS (see above) and treated with 100 ug of either do or $d_8$ ICAT reagent for 90 minutes at room temperature in the dark. The reaction was quenched by the addition of 1 ul mercaptoethanol for 30 minutes at room temperature, and separate do and $d_8$ reactions were mixed together following the quench. Excess ICAT reagent was removed by acetone precipitation and the pelleted protein was suspended in 50 mm ammonium bicarbonate, and digested with 2 ug trypsin overnight at 37° C. with constant vortexing. The sample was boiled for 10 minutes, 100 ul 2×PBS was added, and the pH was adjusted to 5 with 5 ul 3 M sodium acetate prior to loading on the monomeric avidin column.

200 ul of a 50% slurry of monomeric avidin beads were placed in a BioRad mini column, washed twice with 1 ml of 30% acetonitrile with 0.4% TFA, followed by 1.2 ml of 2×PBS pH 7.2. To block tetrameric avidin sites, the column was washed with 0.6 ml 2 mM biotin in PBS, washed with 0.6 ml 100 mM glycine pH 2.8, and washed further with 1.2 ml 2×PBS to return the column to pH 7.2. After plugging the column, the sample (300 ul total volume) was incubated with the beads for 20 minutes with occasional mixing. The column was drained, washed with 1 ml 2×PBS, then 1 ml 1×PBS, followed with a wash of 1.25 ml of 50 mm ammonium bicarbonate in 20% methanol. The retentate was eluted with 0.8 ml of 30% acetonitrile containing 0.4% TFA.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for incorporating a stable isotope into a protein or peptide fragment, comprising:
    (a) reacting a cysteinyl residue in a protein or peptide fragment with an affinity reagent to provide an affinity-labeled protein or peptide fragment, wherein the affinity reagent is coupled to the cysteinyl residue through a cleavable linkage;
    (b) isolating the affinity-labeled protein or peptide fragment on a solid phase;
    (c) releasing the protein or peptide fragment from the solid phase by cleaving the cleavable linkage; and
    (d) reacting the released protein or peptide fragment with an agent comprising one or more stable isotopes to provide a stable isotopically-labeled protein or peptide fragment.

2. The method of claim 1, wherein the cleavable linkage is a disulfide linkage.

3. The method of claim 1, wherein the affinity reagent is a biotinylation reagent.

4. The method of claim 1, wherein the affinity reagent is N-[6-(biotinamido)hexyl]-3'-(2'-pyridyldithio)propionamide.

5. The method of claim 1, wherein the agent is N-ethyl iodoacetamide.

6. The method of claim 1, wherein the agent having one or more stable isotopes is N-ethyl-$d_5$ iodoacetamide.

7. A method for incorporating a stable isotope into a protein or peptide fragment, comprising:
    (a) reacting a cysteinyl residue in a protein or peptide fragment with an affinity reagent to provide an affinity-labeled protein or peptide fragment, wherein the affinity reagent is coupled to the cysteinyl residue through a cleavable linkage;
    (b) isolating the affinity-labeled protein or peptide fragment on a solid phase;
    (c) regenerating the protein or peptide fragment by release from the solid phase by cleaving the cleavable linkage; and
    (d) reacting the cysteinyl residue of the regenerated protein or peptide fragment with an agent comprising one or more stable isotopes to provide a stable isotopically-labeled protein or peptide fragment.

8. The method of claim 7, wherein the cleavable linkage is a disulfide linkage.

9. The method of claim 7, wherein the affinity reagent is a biotinylation reagent.

10. The method of claim 7, wherein the affinity reagent is N-[6-(biotinamido)hexyl]-3'-(2'-pyridyldithio)propionamide.

11. The method of claim 7, wherein the agent is N-ethyl iodoacetamide.

12. The method of claim 7, wherein the agent having one or more stable isotopes is N-ethyl-$d_5$ iodoacetamide.

* * * * *